United States Patent
Wang et al.

(10) Patent No.: US 10,338,034 B2
(45) Date of Patent: Jul. 2, 2019

(54) TRANSDUCER DEVICE COMPRISING AN INSULATING FILM BETWEEN A THROUGH WIRING LINE AND A SEMICONDUCTOR SUBSTRATE

(71) Applicant: CANON KABUSHIKI KAISHA, Tokyo (JP)

(72) Inventors: Shinan Wang, Komae (JP); Yutaka Setomoto, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 220 days.

(21) Appl. No.: 14/978,526

(22) Filed: Dec. 22, 2015

(65) Prior Publication Data
US 2016/0187299 A1 Jun. 30, 2016

(30) Foreign Application Priority Data
Dec. 25, 2014 (JP) .................. 2014-262664

(51) Int. Cl.
*G01N 29/24* (2006.01)
*B06B 1/06* (2006.01)
(Continued)

(52) U.S. Cl.
CPC ....... *G01N 29/2406* (2013.01); *B06B 1/0292* (2013.01); *B06B 1/0644* (2013.01);
(Continued)

(58) Field of Classification Search
CPC ....... G01N 21/1702; G01N 2021/1704; G01N 2021/1706; G01N 29/24; G01N 29/2406;
(Continued)

(56) References Cited

U.S. PATENT DOCUMENTS

| 5,136,172 A * | 8/1992 | Nakata ............... G01N 21/1702 |
| | | 250/559.39 |
| 7,018,020 B2 * | 3/2006 | Hayakawa ........... B41J 2/14129 |
| | | 257/276 |

(Continued)

FOREIGN PATENT DOCUMENTS

| CN | 101378605 A | 3/2009 |
| CN | 101714512 A | 5/2010 |

(Continued)

*Primary Examiner* — Natalie Huls
(74) *Attorney, Agent, or Firm* — Canon U.S.A. Inc., IP Division

(57) ABSTRACT

A method for creating an electronic device including a semiconductor substrate, an element unit, a through wiring line, and a wiring portion includes forming interstitial via holes in a first surface of the substrate, forming a first insulating film on the inner walls of the via holes, forming openings that reach the first insulating film on the bottoms of the via holes from a second surface of the substrate, forming a second insulating film on the bottoms of the openings, forming a through wiring line in the via holes, forming an element unit that electrically connects the through wiring line, reducing the thickness of the substrate from the second surface so that the second surface becomes flush with the second insulating film on the bottoms of the openings, and forming a wiring portion, on the second insulating film, that electrically connects to the through wiring line.

18 Claims, 8 Drawing Sheets

(51) Int. Cl.
  *B06B 1/02* (2006.01)
  *B81C 1/00* (2006.01)
(52) U.S. Cl.
  CPC ..... *B81C 1/00158* (2013.01); *G01N 29/2418* (2013.01); *G01N 29/2437* (2013.01)
(58) Field of Classification Search
  CPC .............. G01N 29/2418; B06B 1/0292; H01L 21/76898; H01L 2225/06541
  See application file for complete search history.

(56) References Cited

U.S. PATENT DOCUMENTS

| | | | | |
|---|---|---|---|---|
| 8,299,624 | B2* | 10/2012 | Matsuo | H01L 21/6835 257/773 |
| 9,394,162 | B2* | 7/2016 | Rothberg | B81C 1/00238 |
| 2005/0221601 | A1* | 10/2005 | Kawano | H01L 21/76898 438/622 |
| 2006/0148250 | A1* | 7/2006 | Kirby | H01L 21/76898 438/667 |
| 2007/0085189 | A1* | 4/2007 | Sunohara | H01L 21/568 257/686 |
| 2008/0054444 | A1 | 3/2008 | Tuttle | |
| 2008/0079121 | A1* | 4/2008 | Han | H01L 21/76898 257/621 |
| 2008/0136038 | A1* | 6/2008 | Savastiouk | H01L 21/76898 257/774 |
| 2008/0283945 | A1* | 11/2008 | Kobayashi | B06B 1/0292 257/416 |
| 2009/0008747 | A1* | 1/2009 | Hoshino | H01L 21/6835 257/621 |
| 2010/0244251 | A1* | 9/2010 | Torazawa | H01L 21/76805 257/741 |
| 2010/0283130 | A1* | 11/2010 | Nishio | H01L 21/76898 257/621 |
| 2011/0088453 | A1* | 4/2011 | Nicoletti | B82Y 15/00 73/24.02 |
| 2012/0262770 | A1* | 10/2012 | Torashima | G01N 29/2418 359/199.2 |
| 2013/0061678 | A1* | 3/2013 | Yamamoto | A61B 5/0095 73/602 |
| 2013/0255389 | A1* | 10/2013 | Watanabe | G01N 29/2418 73/655 |
| 2014/0102204 | A1* | 4/2014 | Akiyama | G01N 29/2406 73/655 |
| 2014/0145275 | A1* | 5/2014 | Hong | B06B 1/0292 257/416 |
| 2014/0182384 | A1* | 7/2014 | Watanabe | A61B 5/0095 73/655 |
| 2014/0318255 | A1* | 10/2014 | Torashima | B06B 1/0292 73/627 |
| 2015/0101395 | A1* | 4/2015 | Dehe | G01N 29/2418 73/24.02 |
| 2015/0115412 | A1* | 4/2015 | Nomura | H01L 23/481 257/621 |
| 2015/0183634 | A1* | 7/2015 | Wang | B06B 1/0292 73/643 |
| 2016/0043660 | A1* | 2/2016 | Wang | B81C 1/00134 73/780 |
| 2016/0091344 | A1* | 3/2016 | Hasegawa | B06B 1/0292 73/658 |
| 2016/0144402 | A1* | 5/2016 | Kandori | B06B 1/0292 73/632 |
| 2016/0153939 | A1* | 6/2016 | Kato | G01N 29/2406 73/606 |
| 2017/0008030 | A1* | 1/2017 | Dekker | B06B 1/0292 |
| 2017/0067859 | A1* | 3/2017 | Kolb | G01N 29/30 |
| 2017/0156209 | A1* | 6/2017 | Wang | G01N 29/2406 |
| 2017/0167970 | A1* | 6/2017 | Wang | B06B 1/0292 |
| 2017/0168025 | A1* | 6/2017 | Wang | G01N 29/2406 |
| 2017/0221817 | A1* | 8/2017 | Nomura | H01L 23/5283 |
| 2017/0315099 | A1* | 11/2017 | Rothberg | B81C 1/00238 |
| 2017/0326589 | A1* | 11/2017 | Sudol | B06B 1/0292 |
| 2017/0333945 | A1* | 11/2017 | Torashima | B06B 1/0292 |

FOREIGN PATENT DOCUMENTS

| | | |
|---|---|---|
| CN | 102686018 A | 9/2012 |
| CN | 103347620 A | 10/2013 |
| CN | 103908226 A | 7/2014 |
| CN | 103989455 A | 8/2014 |
| JP | 2012-195514 A | 10/2012 |
| JP | 2013-126070 A | 6/2013 |

* cited by examiner

TRANSDUCER DEVICE COMPRISING AN INSULATING FILM BETWEEN A THROUGH WIRING LINE AND A SEMICONDUCTOR SUBSTRATE

BACKGROUND OF THE INVENTION

Field of the Invention

The present invention relates to a method for creating a device, such as an electronic device and a micro-electro-mechanical system (MEMS) device, with a through wiring line.

Description of the Related Art

Faster high-performance systems of integrated circuits, typified by LSIs, are required. To achieve faster higher-performance systems of integrated circuits, chip mount technology using a three-dimensional structure is required. For this purpose, a through wiring line capable of electrically connecting chips in the shortest distance is used. In this case, the through wiring line and other electrical wiring lines need an insulating film having sufficient insulating properties between the lines and the substrate. In particular, an electronic device that needs high drive voltage or output voltage needs to have high insulation performance among the electrodes, the wiring lines, and the substrate.

Some electronic devices need a thin substrate to meet performance requirements. For example, for ultrasonic transducers, a desired thickness of the substrate is smaller or equal to half the wavelength of ultrasonic waves to reduce the influence of reflection from the substrate on device performance. In an example, the substrate, if made of silicon, of an ultrasonic transducer with a frequency of about 20 KHz on a higher frequency side has, preferably, thickness of about 250 µm or less. To create an electronic device with a thin substrate, there are a technique using a thin substrate with a desired thickness from the beginning of the creating process and a technique using a substrate thicker than a desired thickness at the beginning of the creating process.

The former method needs to obtain necessary mechanical strength by bonding the thin substrate to a support substrate to prevent the substrate from being deformed or broken during creation. The need for the support substrate increases as the diameter of the thin substrate for use in creation increases. In this case, the creating process can be significantly limited according to the method of bonding the thin substrate and the support substrate. For example, when the thin substrate and the support substrate are bonded together using an adhesive, usable chemicals and the maximum temperature for the creating process are limited according to the resistance of the adhesive to the chemicals and temperature. In the latter method, the first half of the creating process is performed using a thick substrate, but the substrate is decreased to a desired thickness during the latter half of the creating process. In this case, the first half of the creating process has high flexibility.

Japanese Patent Laid-Open No. 2012-195514 discloses a technique for performing the first half of the creating process using a substrate with a thickness larger than a desired thickness and decreasing the thickness of the substrate to a desired thickness during the latter half of the creating process. In this technique, interstitial via holes are formed in a base substrate, an insulating film is formed on the inner walls of the via holes, and then an element unit is formed. After the base substrate is decreased in thickness, and an insulating film is formed on the ground surface of the thinned substrate, a through wiring line is formed. In this case, since the insulating film is formed on the inner walls of the via holes before the element unit is formed, the insulating film can be formed at a sufficiently high temperature (for example, 800° C. or higher). This allows an insulating film having high dielectric strength to be formed on the inner walls of the via holes. This is because a higher-quality insulating film can be formed by high-temperature deposition than that by low-temperature deposition. It is known that, for example, a silicon thermal oxide film formed by thermal oxidation at 800° C. or higher has higher denseness, higher uniformity in thickness, and higher dielectric strength than a silicon oxide film formed by Chemical Vapor Deposition (CVD) at 400° C. or less.

However, the method disclosed in Japanese Patent Laid-Open No. 2012-195514 needs to remove an insulating film on the back of the substrate after elements are formed and to form an insulating film again to form a thin substrate. The insulating film to be formed on the back of the substrate again is formed, preferably, at 400° C. or less, to prevent damage to the element unit on the substrate. This can cause the dielectric strength of the insulating film on the back of the substrate to be insufficient for the device that needs high voltage.

SUMMARY OF THE INVENTION

According to an aspect of the present invention, there is provided a method for creating a device including an element portion including electrodes, a substrate including a first surface and a second surface opposite to the first surface, and a through wiring line extending from the first surface to the second surface. The electrodes are electrically connected to the through wiring line. The method includes the steps of forming first holes from the first surface of the substrate, the first holes having a depth with which the first holes do not pass through the substrate; forming a first insulating film on inner walls of the first holes; forming second holes that reach the first insulating film from the second surface of the substrate opposite to the first insulating film; forming a second insulating film on the second holes; injecting a material of the through wiring line into the first holes; forming the element portion on the first surface, the element portion electrically connecting to the material of the through wiring line; thinning the substrate from the second surface of the substrate to the second insulating film; and forming a wiring portion on the second insulating film, the wiring portion connecting to the material of the through wiring line.

The method allows insulating films to be formed on the inner walls of the via holes in which the through wiring line is formed and on the back of the substrate corresponding to substrate backwiring lines before the through wiring line and the element portion are formed, regardless of the thickness of the substrate of the device. This allows the insulating films to be formed using a high-temperature deposition technique, thus providing high insulation resistance This provides various devices including an electronic device with high electrical reliability. The method is effective particularly in enhancing the electrical, reliability of thin substrate device, which has been difficult to achieve. According to another aspect of the present invention, an electronic device is created in order of interstitial via holes and the through wiring line in an insulating substrate, and then an element portion. This allows an insulating substrate with sufficiently high insulation resistance to be used, thus providing an electronic device with high electrical reliability.

Further features of the present invention will become apparent from the following description of exemplary embodiments with reference to the attached drawings.

DESCRIPTION OF THE EMBODIMENTS

Figure 1A:
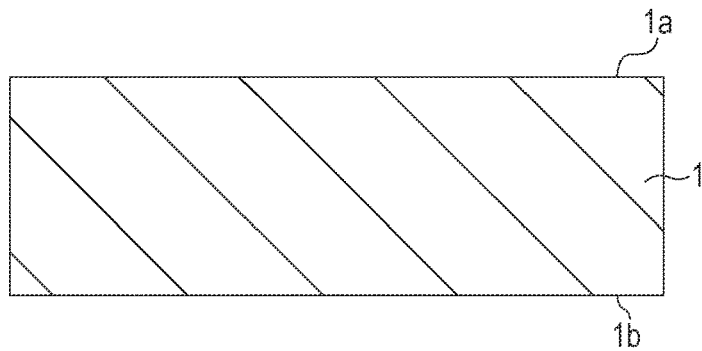
FIG. 1A is a cross-sectional view of an electronic device illustrating an example of a method of creation according an embodiment of the present invention.

Methods for creating a device according to embodiments the present invention include a method using a semiconductor substrate as a substrate and a method using an insulating substrate as a substrate. First, the method using a semiconductor substrate will be described.

Interstitial via holes for through wiring lines are formed from a first surface of the semiconductor substrate. Next, a first insulating film is formed on the surface of the substrate including the inner walls of the via holes. Next, openings that reach the first insulating film on the bottoms of the via holes are formed from a second surface opposite to the first surface of the substrate, and then a second insulating film is formed on the bottoms of the openings. Next, through wiring lines are formed in the via holes. Next, an element unit to be electrically connected to the through wiring lines is formed on the first surface. Next, the substrate is reduced in thickness from the second surface so that the second surface become substantially flush with the second insulating film on the bottoms of the openings. Next, wiring portions that electrically connect to the through wiring lines are formed on the second insulating film by, for example, forming openings in the second insulating film so as to expose the end faces of the through wiring lines adjacent to the second surface. In the embodiment in which an insulating substrate is used, interstitial via holes are formed in a first surface of two opposing surfaces of the substrate. Next, openings are formed from a second surface of the opposing surfaces of the substrate so that the substrate material on the bottoms of the is holes remains. Next, through wiring lines are formed in the via holes. Next, an element unit that electrically connects to the through wiring lines is formed on the first surface. Next, the substrate is reduced in thickness from the second surface so that the second surface become flush with the substrate material on the bottoms of the openings. Next, wiring portions that electrically connect to the through wiring lines are formed on the substrate material by forming openings in the substrate material so as to expose the end faces of the through wiring lines on the second surface.

While embodiments and examples of the present invention will be described with reference to the drawings, it is to be understood that the embodiments and examples are given for mere illustration and are not intended to limit the present invention and that various modifications and changes can be made within the scope of the invention.

Embodiment

A method for creating an electronic device according to an embodiment of the present invention will be described with reference to FIGS. 1A to 1K. FIGS. 1A to 1J are cross-sectional views of the electronic device according to this embodiment, and FIG. 1K is a plan view of the electronic device. Although a plurality of elements are generally formed on one substrate in the process of creating an electronic device, FIGS. 1A to 1K illustrate a minimum structure constituting one electronic device for illustrative purpose.

First, a substrate 1 is prepared, as illustrated in FIG. 1A. The substrate 1 is a semiconductor substrate. For example, the substrate 1 is a silicon substrate. The substrate 1 includes a first surface 1a and a second surface 1b at the opposite side from the first surface. The first surface 1a and the second surface 1b may be parallel to each other. The substrate 1 has a thickness of 350 μm to 1,000 μm, for example. A method for creating the substrate 1 will be described using an example in which the substrate 1 is a silicon substrate. The silicon substrate has the advantage of being easy processed as compared with substrates made of other materials.

Figure 1B:
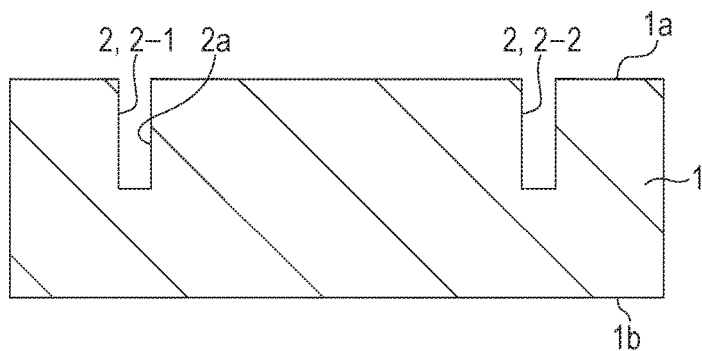
FIG. 1B is a cross-sectional view of the electronic device.

Next, interstitial via holes 2 (including 2-1 and 2-2) for accommodating through wiring lines 6 (see FIG. 1F) are formed from the first surface 1a of the substrate 1, as illustrated in FIG. 1B. This corresponds to first holes having a depth that does not pass through the substrate 1. The shape, number, and disposition of the via holes 2 are defined by photolithography according to the application. The via holes 2 have a diameter of 20 μm to 100 μm and are arrayed at a pitch of 200 μm in a lateral direction and a pitch of 2 mm in a longitudinal direction. The depth of the via holes 2 is substantially the same as the thickness of the final substrate 1 of the electronic device, for example, 10 μm to 300 μm (that is, 300 μm or less). In forming the via holes 2, the substrate 1 is processed using a photoresist pattern (not shown) defined by photolithography as an etching mask, for example. The via holes 2 are formed using, for example, a reactive ion etching (RIE) technique. After the via holes 2 are formed, the etching mask is removed using an appropriate technique. The via holes 2 may have smooth inner walls 2a to achieve high electrical insulation. For example, the surface roughness of the inner walls 2a of the via holes 2 is preferably 50 nm or less at the maximum height Rmax.

If the inner walls 2a of the via holes 2 are not sufficiently smooth after the RIE, the inner walls 2a is subjected to a smoothing process. For example, a silicon oxide film is formed on the surface of the inner wall 2a, and then the silicon oxide film is removed using a chemical, such as hydrogen fluoride and buffered hydrogen fluoride ((BHF). This allows the inner walls 2a to be smoothed. Heating the inner walls 2a in a hydrogen atmosphere is also effective in smoothing the inner walls 2a. The smoothing process is performed a plurality of times as needed.

Figure 1C:
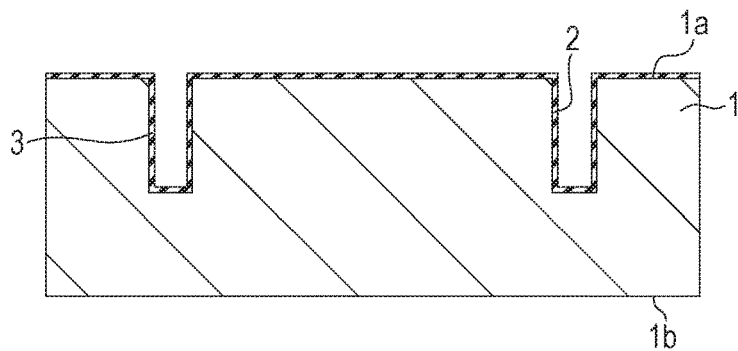
FIG. 1C is a cross-sectional view of the electronic device.

Next, as illustrated in FIG. 1C, a first insulating film 3 is formed on the inner walls 2a of the via holes 2 (see FIG. 1B). The first insulating film 3 may be a film having high dielectric strength. For that purpose, the first insulating film 3 is formed at a high temperature. Examples of the first insulating film 3 include a silicon thermal oxide film formed by thermal oxidation at 800° C. or higher, a silicon nitride film formed by CVD at 800° C. or higher, and an insulating film formed of two or more layers of these films. The thickness of the first insulating film 3 is determine according to a necessary performance. For example, the thickness of the first insulating film 3 is 0.5 μm to 2.0 μm. A barrier film may be formed on the surface of the first insulating film 3 to prevent the heat of the material of the through wiring lines 6 from diffusing to the substrate 1. The material and the thickness of the barrier film need to be designed in accordance with the materials of the through wiring lines 6, the substrate 1, and the first insulating film 3 and the processing temperature and time. In an example, the barrier film is made of silicon nitride with a thickness of about 100 nm and is formed using a low-pressure CVD (LP-CVD) technique. If the inner walls 2a of the via holes 2 have been smoothed in FIG. 1B, the first insulating film 3 formed on the inner walls 2a has little defect and is resistant to a stress due to heat treatment or another treatment. When the first insulating film 3 is formed on the inner walls 2a of the via holes 2, the same insulating film as the first insulating film 3 may be formed on the first surface 1a and the second surface 1b of the substrate 1 because there is no problem.

Figure 1D:
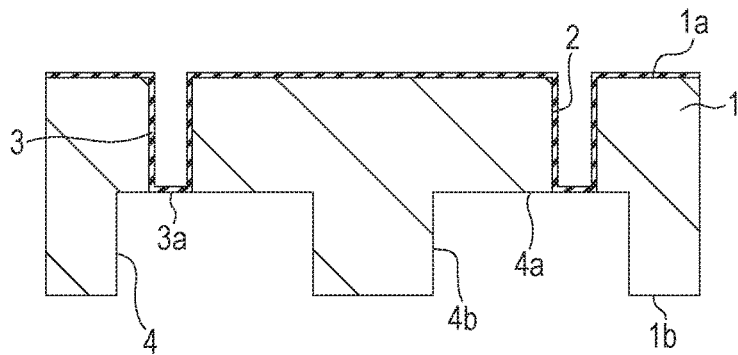
FIG. 1D is a cross-sectional view of the electronic device.

Next, as illustrated in FIG. 1D, openings 4 are formed from the second surface 1b of the substrate 1. The openings 4 correspond to second holes. The shape, area, and disposition of the bottom 4a of each opening 4 are designed so that the bottom 4a includes a portion 3a of the first insulating film 3 on the bottom of the via hole 2 and a wiring line 12 (see FIG. 1J). In other words, the second hole reaches the first insulating film 3. The openings 4 are formed so that the portions 3a of the first insulating film 3 are exposed. The method for forming the openings 4 may be the same as the method for forming the via holes 2. For example, the openings 4 are formed by RIE of silicon. The silicon RIE technique allows silicon to be etched in priority to an insulating film. This allows the openings 4 in FIG. 1D to be easily formed. The bottoms 4a of the openings 4 may be flat, but portions of the bottoms 4a corresponding to the portions 3a of the first insulating film 3 may protrude toward the second surface 1b of the substrate 1. For example, the protrusions have a height of 5 μm or less.

Figure 1E:
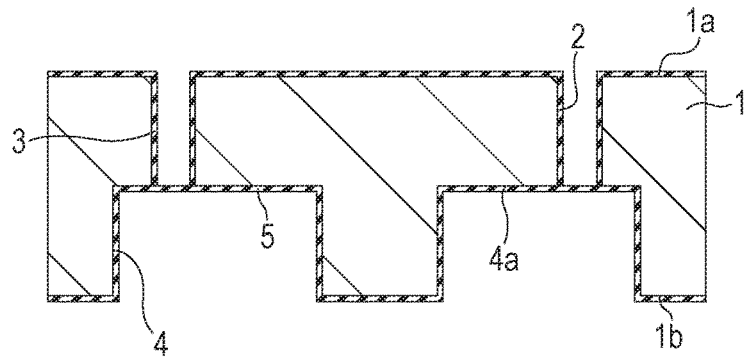
FIG. 1E is a cross-sectional view of the electronic device.

Next, as illustrated in FIG. 1E, a second insulating film 5 is formed on the bottoms 4a of the opening 4 (see FIG. 1D). The second insulating film 5 may be formed like the first insulating film 3. Examples of the second insulating film 5 include a silicon thermal oxide film formed by thermal oxidation at 800° C. or higher, a silicon nitride film formed by CVD at 800° C. or higher, and an insulating film formed of two or more layers of these films. Although the same insulating film as the second insulating film is also formed on the surface of the substrate 1 including side walls 4b of the openings 4 (see FIG. 1D) and the second surface 1b when the second insulating film 5 is formed on the bottoms 4a of the openings 4, there is no problem. If both of the first insulating film 3 and the second insulating film 5 are silicon thermal oxide films, they share the portions 3a.

Figure 1F:
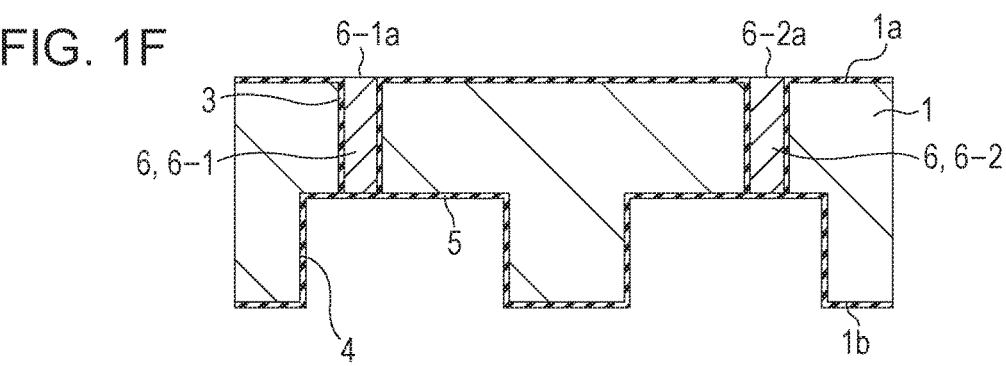
FIG. 1F is a cross-sectional view of the electronic device.

Next, as illustrated in FIG. 1F, the via holes 2 (including 2-1 and 2-2) are filled with a conductive member to form the through wiring lines 6 (including 6-1 and 6-2). In other words, a wiring material is injected. The process of forming the through wiring lines 6 includes, for example, injecting a conductive member and smoothing the end faces of the conductive member by chemical mechanical polishing (CMP). For example, a barrier layer and a seed layer (not shown) are formed in sequence using a CVD technique on the first surface 1a of the substrate 1 including the inner wall 2a of the via holes 2 (the first holes) (see FIG. 1B) and on which the first insulating film 3 is formed. The conductive member is electrolytically plated to fill the via holes 2 by passing current through the seed layer. The plating with the conductive member is electrolytic copper plating using copper sulfate as main liquid. The end faces 6-1a and 6-2a of the conductive member are planarized, and the conductive member, the seed layer, and the barrier layer formed on portions of the substrate 1 other than the first surface 1a are removed by CMP from the first surface 1a of the substrate 1. The end faces 6-1a and 6-2a of the conductive member become substantially flush with the surface of the first insulating film 3 on the first surface 1a of the substrate 1 by the CMP, so that the surfaces are planarized. The conductive member whose end is processed forms the through wiring lines 6.

Figure 1G:
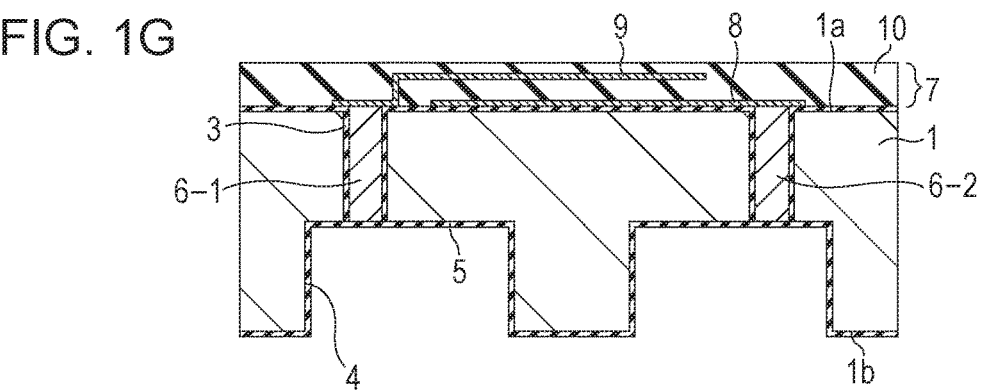
FIG. 1G is a cross-sectional view of the electronic device.

Next, as illustrated in FIG. 1G, an element unit 7 is formed on the first surface 1a of the substrate 1. The element unit 7 includes electrodes (including a first electrode 8 and a second electrode 9) and another portion 10. The electrodes connected to the through wiring lines 6 are respectively overlapped with at least part of the end faces 6-1a and 6-2a of the through wiring lines 6. For example, the first electrode 8 partially overlaps with the end face 6-2a of the through wiring line 6-2 (see FIG. 1F), and the second electrode 9 partially overlaps with the end face 6-1a of the through wiring line 6-1 (see FIG. 1F). Examples of the element unit 7 include various MEMS elements. More specific examples include a capacitive micro-machined ultrasonic transducer (CMUT) and a piezoelectric transducer in which a piezoelectric material is sandwiched between a first electrode and a second electrode. A method for forming the element unit 7 is designed to the specifications of the device. In an example, the CMUT includes a cell including a first electrode, a second electrode disposed across a void from the first electrode, and a diaphragm formed of insulating films disposed above and under the second electrode and supported so as to vibrate.

Figure 1H:
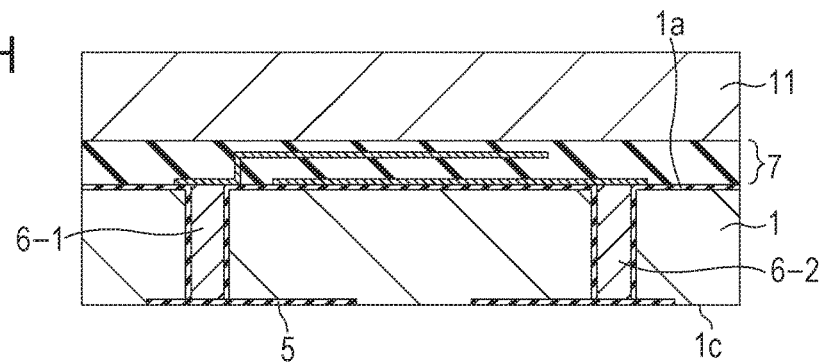
FIG. 1H is a cross-sectional view of the electronic device.
Figure 2A:
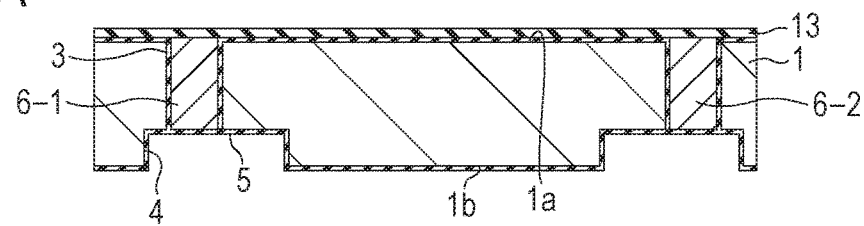
FIG. 2A is a cross-sectional view of a device of a first example illustrating a method of creation.
Figure 2B:
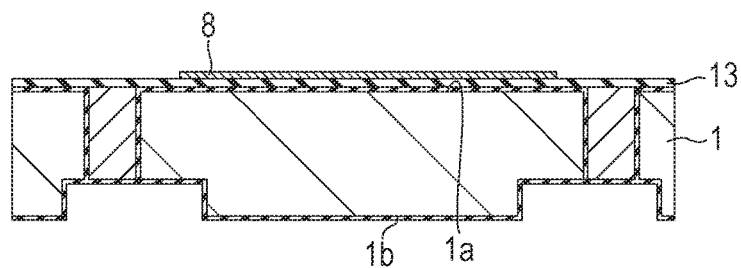
FIG. 2B is a cross-sectional view of the device.
Figure 2C:
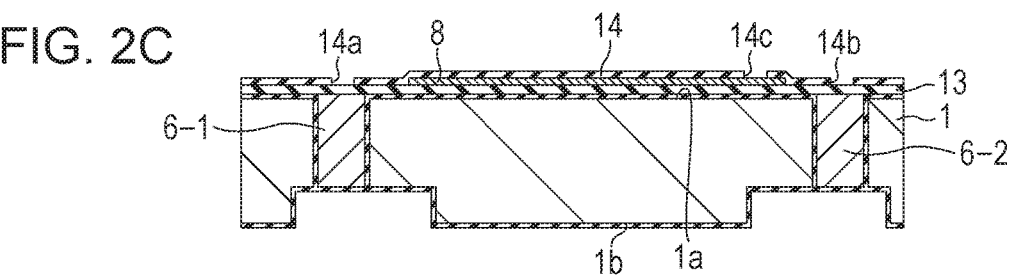
FIG. 2C is a cross-sectional view of the device.
Figure 2D:
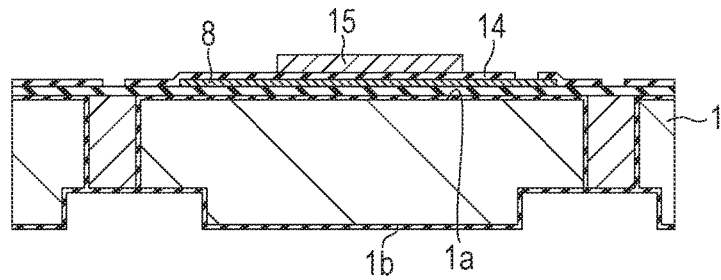
FIG. 2D is a cross-sectional view of the device.
Figure 2E:
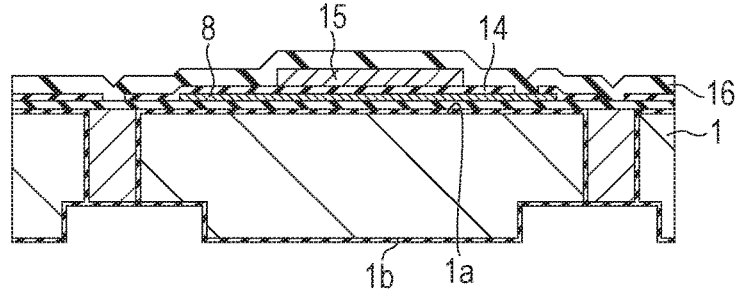
FIG. 2E is a cross-sectional view of the device.
Figure 2F:
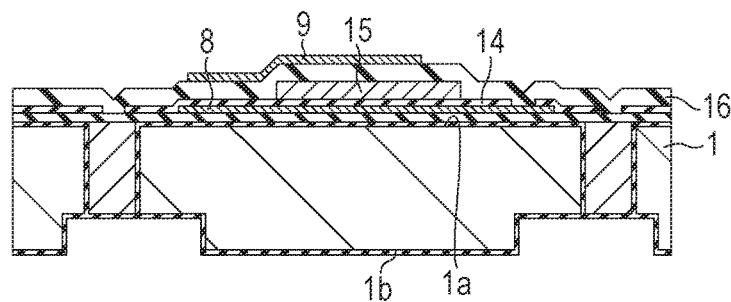
FIG. 2F is a cross-sectional view of the device.
Figure 2G:
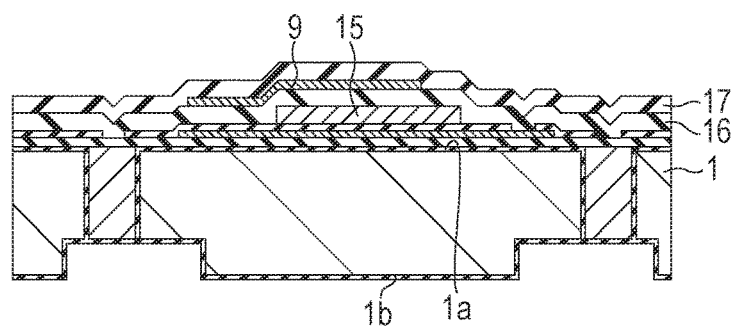
FIG. 2G is a cross-sectional view of the device.

Next, as illustrated in FIG. 1H, the substrate 1 is reduced in thickness so that the second surface 1b of the substrate 1 becomes substantially flush with the second insulating film 5 on the bottoms of the openings 4 (see FIG. 2G). The thickness of the thus-thinned substrate 1 is substantially the same as the depth of the via holes 2 and a desired thickness of the substrate 1 of the electronic device. The new surface 1c of the second surface 1b of the thinned substrate 1 becomes substantially flush with the second insulating film 5. Examples of a method for reducing the thickness of the substrate 1 include grinding, mechanical polishing, and CMP. Reducing the thickness of the substrate 1 decreases the mechanical strength of the substrate 1. Therefore, a support substrate 11 is bonded to the first surface 1a of the substrate 1 before the reduction of the thickness to protect the substrate 1, and the reduction of the thickness is executed in this state. The material of the support substrate 11 and a method of boding may be simple because the thinning process and subsequent creating process do not need heating at 100° C. or higher. For example, the support substrate 11 may be a commercially available substrate polishing tape or a substrate made of glass or silicon which can easily be bonded to or peeled from the substrate 1.

Figure 1I:
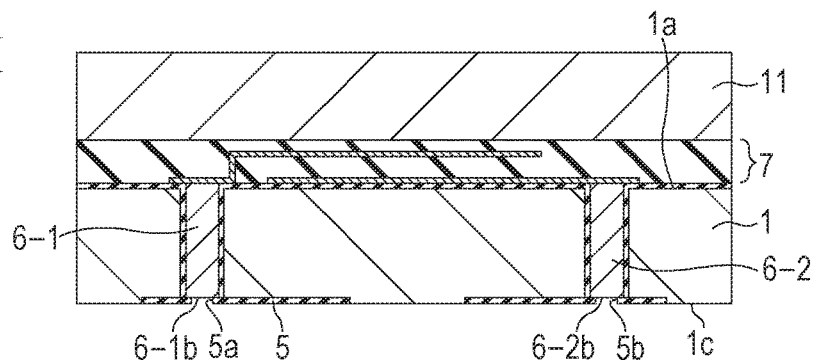
FIG. 1I is a cross-sectional view of the electronic device.

Next, as illustrated in FIG. 1I, openings 5a and 5b are formed in the portions 3a of the first insulating film 3 and the second insulating film 5. Forming the openings 5a and 5b causes the via holes 2 to completely pass through the first surface 1a and the second surface 1b of the substrate 1, allowing the end faces (including 6-1b and 6-2b) of the through wiring lines 6 adjacent to the second surface 1b of the substrate 1 to be exposed. A process for forming the openings 5a and 5b includes forming a mask (not shown) by photolithography and etching the second insulating film 5 and the portions 3a of the first insulating film 3. Examples of a method of etching include plasma etching using reactive gas and etching using a liquid chemical. The barrier layer on the surface of the end faces 6-1b and 6-2b of the through wiring line 6, viewed from the openings 5a and 5b, is removed by etching as needed. Examples of a method for etching the barrier layer include plasma etching using reactive gas and etching using a liquid chemical. If the new surface 1c of the second surface 1b of the substrate 1 is not to be exposed, an low-temperature insulating film may be formed on the new second surface 1c of the substrate 1 before the openings 5a and 5b are formed. For example, before the openings 5a and 5b are formed, a silicon oxide is formed on the new second surface 1c of the substrate 1 by CVD at a temperature of 300° C. In this case, the low-temperature insulating film, described above, at portions corresponding to the openings 5a and 5b is removed to form the openings 5a and 5b.

Figure 1J:
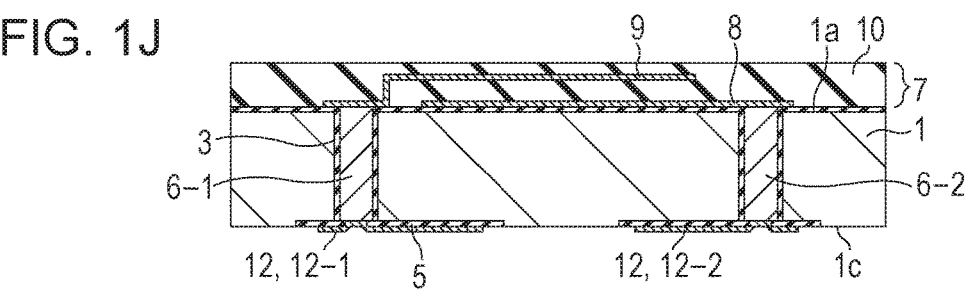
FIG. 1J is a cross-sectional view of the electronic device.
Figure 1K:
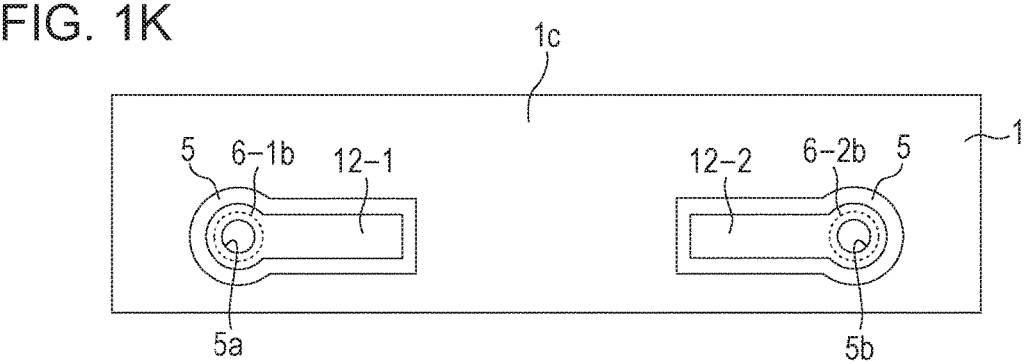
FIG. 1K is a plan view of the electronic device.

Next, as illustrated in FIG. 1J, wiring lines 12 (including 12-1 and 12-2) to be electrically connected to the end faces (including 6-1b and 6-2b) of the through wiring lines 6 are formed. The wiring lines 12 respectively connect to the end faces 6-1b and 6-2b of the through wiring lines 6 through the openings 5a and 5b. The wiring lines 12 except the connecting portions are formed on the second insulating film 5 and are not in contact with the new surface 1c of the second surface 1b of the thinned substrate 1. The wiring lines 12 are formed inside the outer periphery of the second insulating film 5. In other words, as illustrated in the plan view of FIG. 1K, the second insulating film 5 embraces the end face (6-1b or 6-2b) of the through wiring line 6 and the wiring line 12 (12-1 or 12-2). The shortest distance between the outer periphery of the wiring line 12 and the outer periphery of the second insulating film 5 depends on the withstand voltage specification of the element unit 7. In other words, the outer periphery of the wiring line 12 and the outer periphery of the second insulating film 5 are spaced apart from each other so that, when a maximum voltage is applied to the wiring line 12, a leak current between the wiring line 12 and the new surface 1c of the substrate 1 is negligibly weak. Examples of the shortest distance include 1 µm to 10 µm. The wiring lines 12 are mainly made of metal. The wiring lines 12 are formed using a method including metal sputter deposition, forming an etching mask, including photolithography, and etching metal.

After the wiring lines 12 are formed, a dicing tape (not shown) is bonded to the new surface 1c of the second surface 1b of the substrate 1, and then the support substrate 11 (see FIG. 1I) is peeled off. The substrate 1 is divided into devices of a desired size using dicing or another suitable technique. The dicing tape is then peeled off. If the support substrate 11 serves as a dicing tape, there is no need to bond a dicing tape to the new surface 1c. In this case, after the wiring lines 12 are formed, the substrate 1 is divided into devices from the second surface 1b of the substrate 1, and then the support substrate 11 (see FIG. 1I) is peeled off.

Next, the electronic device (including the element unit 7, the through wiring lines 6, and the wiring lines 12) created through the processes from FIGS. 1A to 1J is coupled to a control circuit. The coupling is performed via the wiring lines 12. Examples of a method of coupling include metal direct bonding, bump bonding, anisotropic conductive film (ACE) bonding, and wire bonding.

Thus, the method of creation according to this embodiment allows insulating films having high dielectric strength to be formed between electrodes, through wiring lines, and substrate backwiring lines and the substrate of the device even if the substrate is so thin that it has no mechanical strength necessary for the creating process. This provides the entire device with high electrical reliability. Since the method for creating a device according to this embodiment needs a support substrate only at the last stage of creation, there is little limitation on chemicals and the maximum temperature in the main creating process, thus offering high flexibility in designing the creating process. This makes it easy to optimize the structure of the electronic device and its creating process. The method of creation described above can be applied to various devices including LSI chips and MEMS devices and various systems, thus achieving miniaturization, high-density, and high-functionality of the devices.

If the substrate is an insulating substrate, such as a glass substrate, the processes in FIGS. 1C and 1E are not necessary, and the via holes 2 and the openings 4 may be formed in the substrate 1 in FIG. 1A, as illustrated in FIGS. 1B and 1D. In this case, the via holes 2 are interstitial holes, in which the material of the substrate is left at an appropriate thickness on the bottoms. Thereafter, through wiring lines are formed in the via holes 2, an element unit that is to electrically connect to the through wiring lines is formed on the first surface, the substrate is reduced in thickness from the second surface so that the second surface is flush with the material, of the substrate on the bottoms of the openings 4, and wiring lines that are to electrically connect to the through wiring lines are formed on the substrate material. This is the process of reducing the thickness of the substrate. If the process of reduction is a mechanical process, damage to the element unit and the through wiring lines can be reduced even if the substrate is an insulating substrate.

More specific examples will be described hereinbelow.

First Example

Figure 2H:
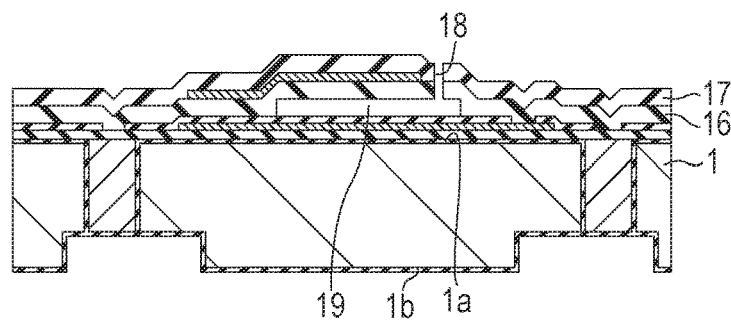
FIG. 2H is a cross-sectional view of the device.
Figure 2I:
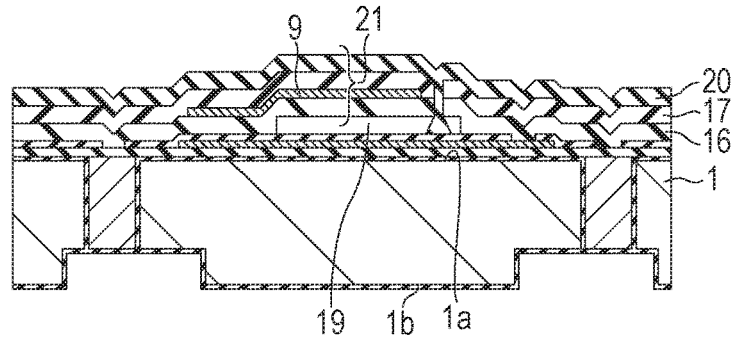
FIG. 2I is a cross-sectional view of the device.
Figure 2J:
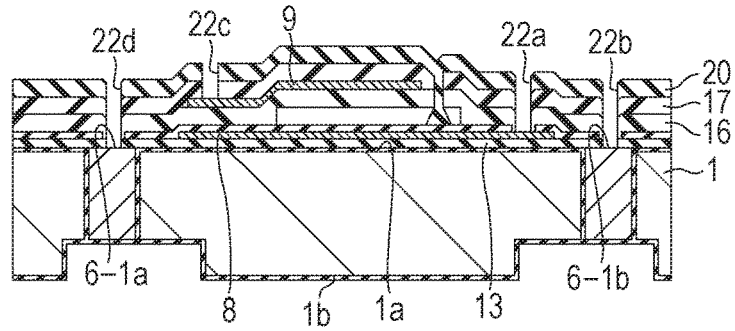
FIG. 2J is a cross-sectional view of the device.
Figure 2K:
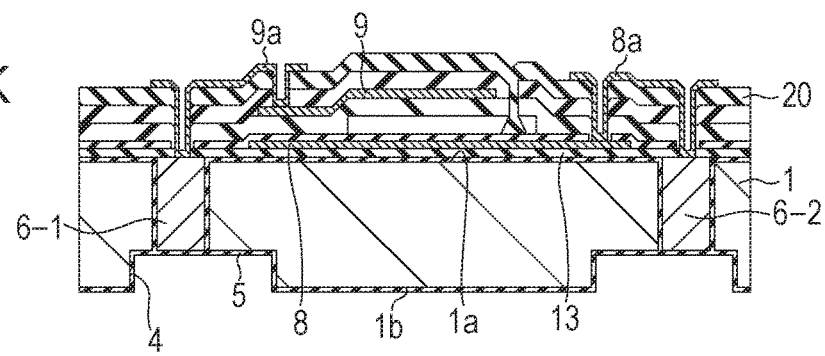
FIG. 2K is a cross-sectional view of the device.
Figure 2L:
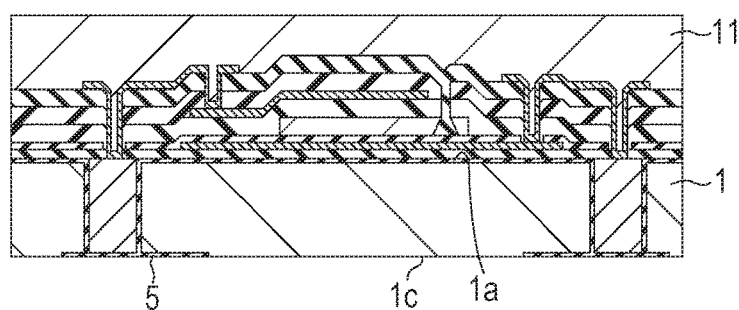
FIG. 2L is a cross-sectional view of the device.
Figure 2M:
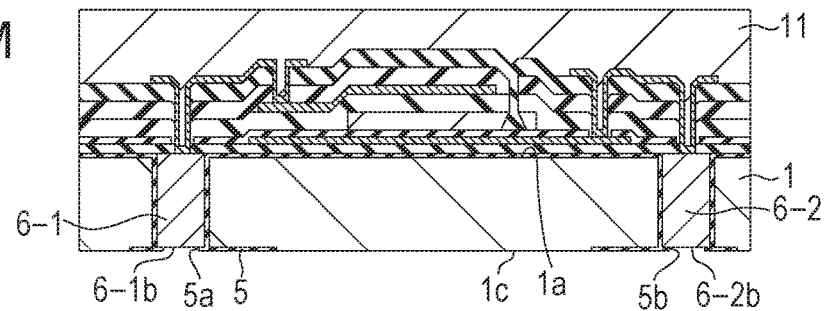
FIG. 2M is a cross-sectional view of the device.
Figure 2N:
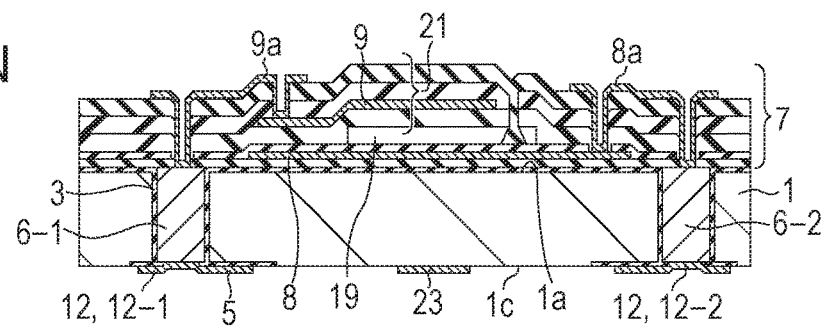
FIG. 2N is a cross-sectional view of the device.
Figure 3A:
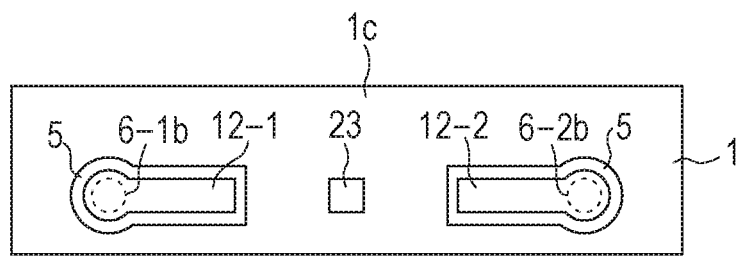
FIG. 3A is a plan view of the device of the first example illustrating a method of creation.
Figure 3B:
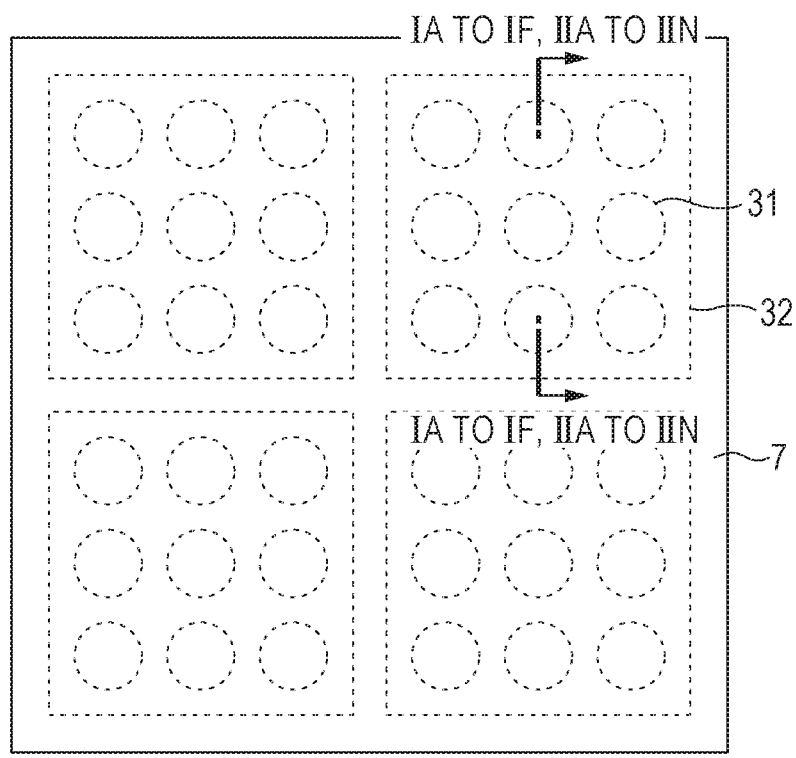
FIG. 3B is a plan view of the device.

Referring to FIGS. 1A to 1F, FIGS. 2A to 2N, and FIGS. 3A and 3B, a method for creating a device of a first example of the present invention will be described. FIGS. 1A to 1F and FIGS. 2A to 2N are cross-sectional views of the device of the first example, and FIGS. 3A and 3B are plan views of the device. The device illustrated here is a what-is-called CMUT. The CMUT can transmit and receive ultrasonic waves using the vibration of a diaphragm and easily obtain broadband characteristics particular in liquid. The element unit 7 of the CMUT includes a large number of cells (also referred to as diaphragms) 31, as illustrated in FIG. 3B. Each of the cells 31 includes a first electrode 8 and a diaphragm 21 including a second electrode 9 disposed with a void 19 from the first electrode 8 (see FIG. 2N). For practical purpose, a plurality of cells 31 constitute an element 32, in which at least one of the first electrodes 8 and the second electrodes 9 are electrically connected across the cells 31.

Some CMUTs include a plurality of elements 32 on a substrate to constitute a single element unit 7 to achieve a desired performance. To independently control the elements 32, it is necessary to form connecting wiring lines corresponding to the individual elements 32. Through wiring lines passing through the substrate may be used to miniaturize the CMUT and reduce the parasitic capacitance of the connecting wiring lines. The simplest configuration includes a pair of through wiring lines connecting to the first electrode and the second electrode for each element. When the CMUT is to be driven, a high voltage of about 200 V is sometimes applied between the first electrode 8 and the second electrode 9. Furthermore, leak current between the electrodes, the through wiring lines, and the substrate backwiring lines and the substrate need to be reduced as much as possible to enhance the performance including the sensitivity of the CMUT. This needs to enhance not only the dielectric strength between the first electrode 8 and the second electrode 9 but also the dielectric strength between the electrodes, the through wiring lines, and the substrate backwiring lines and the substrate as much as possible. The substrate of the CMUT of this example needs a thickness of 250 μm for its frequency response characteristics.

In this example, the structure of the cell in FIGS. 1A to 1F and FIGS. 2A to 2N for use in describing the creating process is illustrated in the cross-sectional view in FIG. 3B taken along line IA-IF (IIA-IIN). For illustrative purpose, only one of the cells 31 (diaphragms) and a pair of through wiring lines of the CMUT are illustrated.

In this example, as illustrated in FIGS. 1A to 1F, first, the substrate 1 including the first insulating film 3, the second insulating film 5, the through wiring lines 6, and the openings 4 is formed. Next, as illustrated in FIGS. 2A to 2N, a CMUT element unit is formed as the element unit 7 on the surface of the substrate 1, and then the wiring lines 12 (including 12-1 and 12-2) are formed on the back of the substrate 1.

As illustrated in FIG. 1A, first, the substrate 1 is prepared. The substrate 1 is a silicon substrate having a diameter of 6 inches, a thickness of 500 μm, and a resistivity of 0.1 Ω·cm. The opposing first surface 1a and second surface 1b of the substrate 1 have the same level of specularity as that of commercially available silicon substrates.

Next, as illustrated in FIG. 1B, the via holes 2 (including 2-1 and 2-2) are formed. The via holes 2 are formed from the first surface 1a of the silicon substrate 1. The via holes 2 have a diameter of 50 μm and a depth of 250 μm. The via holes 2 are formed using a silicon RIE technique using a photoresist pattern (not shown) as an etching mask. After the RIE processing, the inner walls 2a of the via holes 2 are smoothed to have high electrical insulation. In the smoothing process, a silicon oxide film is formed on the surfaces of the inner walls 2a by thermal oxidation, and then the silicon oxide film is removed using buffered hydrogen fluoride, thereby making the surface roughness of the inner walls 2a 50 nm or less at the maximum height (Rmax).

Next, as illustrated in FIG. 1C, the first insulating film 3 is formed on the inner walls 2a of the via holes 2 (see FIG. 1B). The silicon thermal oxide film is formed on the inner walls 2a of the via holes 2 (see FIG. 1B) by thermal oxidation at 1,050° C. to have a first insulating film 3 with high dielectric strength. At that time, the same silicon thermal oxide film is formed on the first surface 1a and the second surface 1b of the substrate 1; however, there is no problem. Here, the insulating film formed on the second surface 1b is not illustrated. The silicon thermal oxide film, which is formed as the first insulating film 3, is formed at a uniform thickness of about 1 μm on the inner walls 2a (see FIG. 1B).

Next, as illustrated in FIG. 1D, the openings 4 are formed from the second surface 1b opposed to the first surface 1a of the substrate 1. The shape, area, and disposition of the bottom 4a of each opening 4 are designed so that the bottom 4a includes the portion 3a of the first insulating film 3 on the bottom of the via hole 2 and the wiring line 12 (12-1 or 12-2, see FIG. 2N). The openings 4 are formed using a silicon RIE technique so that the portions 3a of the first insulating film 3 are exposed. The depth of the openings 4 is about 250 μm because the thickness of the silicon substrate 1 is 500 μm, and the depth of the via holes 2 is 250 μm. The silicon thermal oxide film of the second surface 1b at portions corresponding to the openings 4 is removed by BHF etching before the silicon RIE.

Next, as illustrated in FIG. 1E, the second insulating film 5 is formed on the bottoms 4a of the openings 4. The second insulating film 5 is a silicon thermal oxide film formed like the first insulating film 3 and has a thickness of about 1 μm. Although the silicon thermal oxide film is formed also on the surface of the substrate 1 including the side walls 4b of the openings 4 (see FIG. 1D) and the second surface 1b, there is no problem. Since both of the first insulating film 3 and the second insulating film 5 are silicon thermal oxide films, they share the portions 3a.

Next, as illustrated in FIG. 1F, the via holes 2 (including 2-1 and 2-2) are filled with a conductive member to form the through wiring lines 6 (including 6-1 and 6-2). First, a copper thin film (not shown), which is a conductive material, is formed on the surface of the first insulating film 3 formed on the inner walls 2a of the via holes 2. The copper thin film is formed using a CVD technique and has a thickness of about 0.1 μm. The copper thin film is also formed on thermal oxide film on the first surface 1a of the substrate 1 (not shown). The via holes 2 are filled with the conductive member (copper) by electrolytic plating using the copper thin film as a seed layer. Furthermore, the end faces 6-1a and 6-2a of the conductive member are planarized, and the copper plated film and the seed layer formed on portions of the substrate 1 other than the first surface 1a are removed by CMP from the first surface 1a of the substrate 1. The end faces 6-1a and 6-2a of the conductive member become substantially flush with the surface of the first insulating film 3 on the first surface 1a of the substrate 1 by the CMP, so that the surfaces are planarized. The conductive member whose end is thus processed forms the through wiring lines 6.

Next, as illustrated in FIG. 2A, an insulating film 13 is formed on the first surface 1a of the substrate 1. The insulating film 13 coats the end faces 6-1a and 6-2a of the through wiring lines 6 (see FIG. 1F). One of the roles of the insulating film 13 is to protect the end faces 6-1a and 6-2a of the through wiring lines 6 from the subsequent creating process. The insulating film 13 prevents liquid chemicals, reactive gas, ions, and plasma used in the subsequent creating process from eroding the end faces 6-1a and 6-2a of the through wiring lines 6. This allows the quality of the through wiring lines 6 to be maintained, thus exerting no negative effect on the electrical reliability of the entire device. The insulating film 13 is a silicon nitride film with a thickness of 200 nm, which is formed using a PE-CVD (plasma enhanced CVD) technique at a substrate temperature of about 300° C.

Next, as illustrated in FIG. 2B, the first electrode 8 is formed on the insulating film 13. The first electrode 8 is a lower electrode for driving the diaphragm. 21 of the cell 31 of the CMUT (see FIG. 2N). Since the first electrode 8 is formed on the silicon thermal oxide film 3 and the insulating film 13 on the first surface 1a of the substrate 1, the first electrode 8 is insulated from the substrate 1 The first electrode 8 is located below the vibrating portion of the diaphragm 21 of the cell 31 (corresponding to the void 19 in FIG. 2N). The first electrode 8 extends to the periphery from the vibrating portion of the diaphragm 21. The first electrode 8 is configured to electrically conduct to the cells 31 in the element 32. The first electrode 8 is a lamination of a titanium film with a thickness of about 10 nm and a tungsten film with a thickness of about 50 nm. The first electrode 8 is formed using a method including depositing metal, forming an etching mask including photolithography, and etching the metal with a chemical.

Next, as illustrated in FIG. 2C, an insulating film 14 is formed. The insulating film 14 coats the surface of the first electrode 8, one of the roles of which is to serve as an insulating protection film for the first electrode 8. The insulating film 14 is a silicon oxide film with a thickness of 200 nm. The silicon oxide film is formed by CVD at a substrate temperature of about 300° C. After the silicon oxide is deposited, openings 14a, 14b, and 14c that reach the insulating film 13 are formed in the insulating film 14. The openings 14a, 14b, and 14c are formed using a method including forming an etching mask including photolithography and dry etching including reactive ion etching. The openings 14a, 14b, and 14c are cylindrical holes with a diameter of 45 μm, for example.

Next, as illustrated in FIG. 2D, a sacrifice layer pattern 15 is formed. The sacrifice layer pattern 15 is for forming the void 19 (see FIG. 2N) in the cell 31 and is formed with chromium. The thickness of the chromium is determined according to the height of the void 19 required for the performance of the cell 31. For example, if the height of the void 19 is 150 nm, a chromium film with a thickness of 150 nm is first formed on the insulating film 14 using an electron beam evaporation technique. Next, the chromium sacrifice layer pattern 15 is formed using a method including photolithography and wet etching. In an example, the sacrifice layer pattern 15 has a cylindrical structure having a diameter of about 30 μm and a height of about 150 nm and connecting to an etch hole 18 (see FIG. 2H).

Next, as illustrated in FIG. 2E, an insulating film 16 is formed. The insulating film 16 extends across the lower surface of the second electrode 9 (see FIG. 2N), one of the roles of which is to serve as an insulating protective film for the second electrode 9. The insulating film 16 is a silicon nitride with a thickness of 400 nm. The silicon nitride film is formed at a substrate temperature of about 300° C. using a PE-CVD technique. The silicon nitride for the insulating film 16 is given a tensile stress of about 0.1 GPa by controlling the flow rate of the deposition gas during the deposition,.

Next, as illustrated in FIG. 2F, the second electrode 9 is formed. The second electrode 9 is formed on the insulating film 16 so as to oppose the first electrode 8 and serves as an upper electrode for driving the diaphragm 21 (see FIG. 2N). The second electrode 9 is formed by depositing a titanium film with a thickness of 10 nm and an alloy of aluminum and neodymium with a thickness of 100 nm in sequence. The second electrode 9 is formed using a method including metal sputtering deposition, forming an etching mask including photolithography, and metal etching. The deposition conditions for the second electrode 9 are adjusted to give a tensile stress of 0.4 GPa or less at the completion of the creation of the CMUT. The second electrode 9 is configured to electrically conduct to the cells 31 in the element 32.

Next, as illustrated in FIG. 2G, an insulating film 17 is formed. The insulating film 17 coats the upper surface of the second electrode 9, one of the roles of which is to act as an insulating protective film for the second electrode 9. The insulating film 17 may have the same configuration as that of the insulating film 16 and may be formed using the same technique for the insulating film 16.

Next, as illustrated in FIG. 2H, the etch hole 18 is formed, and then the sacrifice layer pattern 15 (see FIG. 2G) is removed. First, the etch hole 18 is formed. The etch hole 18 is formed using a method including photolithography and reactive ion etching of a silicon nitride. Then, the chromium sacrifice layer pattern 15 (see FIG. 2G) is removed by introducing etching liquid through the etch hole 18. This forms the void 19 having the same shape as that of the sacrifice layer pattern 15 (see FIG. 2G).

Next, as illustrated in FIG. 2I, a thin film 20 is formed. The thin film 20 seals the etch hole 18 (see FIG. 2H) and constitutes the vibratable diaphragm 21 above the void 19 together with the insulating film 16, the second electrode 9, and the insulating film 17. An example of the thin film 20 is a silicon nitride with a thickness of 500 nm. The thin film 20 is formed at a substrate temperature of about 300° C. using the PE-CVD technique like the insulating film 16. The thus-formed diaphragm 21 has a tensile stress of about 0.7 GPa as a whole and is configured to cause no sticking, no buckling, and little breakage. In the above creating process, the surface of the lower film is subjected to plasma treatment before the upper film is formed to enhance the inter-film contact of the insulating films 16, 17, and 20. This plasma treatment makes the surface of the lower film clean and active to enhance the inter-film contact.

Next, as illustrated in FIG. 2J, contact holes 22 (including 22a, 22b, 22c, and 22d) for electrical connection are formed. The contact holes 22d and 22b are openings that respectively partially expose the end faces 6-1a and 6-1b of the through wiring lines 6. The contact holes 22a and 22c are openings that respectively partially expose the surfaces of the first electrode 8 and the second electrode 9. The contact holes 22 are formed using a method including forming an etching mask including photolithography and reactive ion etching a silicon nitride. The contact holes 22 are cylindrical holes with a diameter of about 40 μm, for example.

Next, as illustrated in FIG. 2K, connecting wiring lines 8a and 9a are formed adjacent to the first surface 1a of the substrate 1. The connecting wiring lines 8a and 9a are formed by depositing a titanium film with a thickness of 10 nm and an aluminum film with a thickness of 500 nm in this order. The connecting wiring line 8a connects the first electrode 8 and the through wiring line 6-2 via the contact holes 22a and 22b (see FIG. 2J). The connecting wiring line 9a connects the second electrode 9 and the through wiring line 6-1 via the contact holes 22c and 22d (see FIG. 2J). This allows the first electrode 8 adjacent to the first surface 1a of the substrate 1 to be led out to the opposing second surface 1b of the substrate 1 via the through wiring line 6-2. Similarly, the second electrode 9 adjacent to the first surface 1a of the substrate 1 out to the opposing second surface 1b of the substrate 1 via the through wiring line 6-1.

Next, as illustrated in FIG. 2L, the substrate 1 is reduced in thickness so that the second surface 1b of the substrate 1 becomes substantially flush with the second insulating film 5 on the bottoms of the openings 4 (see FIG. 2J). This allows the thickness of the thinned substrate 1 to be substantially the same as the depth of the via holes 2, substantially equal to a desired thickness of 250 μm. The new surface 1c of the second surface 1b of the thinned substrate 1 (see FIG. 2L) becomes substantially flush with the second insulating film 5. The reduction of the thickness is performed using mechanical polishing and CMP. The mechanical polishing is used for high-speed polishing of the substrate 1, and the CMP is used to enhance the flatness of the mechanically polished substrate surface 1c. The surface roughness of the new surface 1c of the second surface 1b is 1 nm or less at Rmax. Before the mechanical polishing and the CMP, a commercially available substrate polishing tape is bonded as a support substrate 11 to the first surface 1a of the substrate 1 to protect the substrate 1. The substrate polishing tape can easily be bonded to the first surface 1a of the substrate 1 on which the CMUT element unit, or the element unit 7, is formed, because the first surface 1a has a roughness of 3 μm or less. The substrate 1 to which the tape is bonded has a parallelism sufficient for reduction in thickness.

Next, as illustrated in FIG. 2M, the openings 5a and 5b are formed at the portions 3a of the first insulating film 3 and the second insulating film 5. Forming the openings 5a and 5b makes the via holes 2 through holes passing through the first surface 1a and the second surface 1b of the substrate 1, exposing the end faces (including 6-1b and 6-2b) of the through wiring lines 6 on the second surface 1b of the substrate 1. The openings 5a and 5b are formed by forming a mask. (not shown) using photolithography and etching the silicon thermal oxide film using BHF. The openings 5a and 5b are cylindrical holes having a diameter of 40 μm, for example.

Next, as illustrated in FIG. 2N, the wiring lines 12 (including 12-1 and 12-2) to be electrically connected to the end faces (including 6-1b and 6-2b) of the through wiring lines 6 are formed. The wiring lines 12 respectively connect to the end faces (including 6-1b and 6-2b) of the through wiring lines 6 (see FIG. 2M) via the openings (5a and 5b) of the second insulating film 5 (see FIG. 2M). The wiring lines 12 except the connecting portions are formed inside the outer periphery of the second insulating film 5 and are not in contact with the new surface 1c of the second surface 1b of the thinned substrate 1. In other words, as illustrated in the plan view of FIG. 3A, the second insulating film 5 embraces the end face (6-1b or 6-2b) of the through wiring line 6 and the wiring line 12 (12-1 or 12-2). The shortest distance between the outer periphery of the wiring line 12 and the outer periphery of the second insulating film 5 is 10 μm, for example. The wiring lines 12 are formed by a method including aluminum sputtering deposition, forming an etching mask including photolithography, and chemical etching of aluminum. The thickness of the aluminum film is about 500 nm.

A ground electrode 23 is formed on the new surface 1c of the second surface 1b of the substrate 1. The ground electrode 23 may be formed at the same time as the wiring line 12 is formed. After the wiring line 12 and the ground electrode 23 are formed, the substrate 1 is divided into elements by dicing to form a CMUT element of a desired size. Then, the polished tape serving as a support substrate 11 (see FIG. 2M) is peeled.

As illustrated in FIG. 2N, the first electrode adjacent to the first surface 1a of the substrate 1 is led out to the wiring line 12-2 on the second surface 1b (1c) of the substrate 1 via the connecting wiring line 8a and the through wiring line 6-2. Likewise, the second electrode 9 adjacent to the first surface 1a of the substrate 1 is led out to the wiring line 12-1 on the second surface 1 (1c) of the substrate 1 via the connecting wiring line 9a and the through wiring line 6-1. The substrate 1 is connected to the ground electrode 23 on the second surface 1b (1c) of the substrate 1.

Furthermore, the CMUT is coupled to a control circuit (not shown). The coupling is performed via the wiring lines 12 (including 12-1 and 12-2). The coupling is performed using ACF bonding. At the same time, the substrate 1 is grounded via the ground electrode 23 to reduce signal noise in driving the CMUT, a bias voltage is applied to the first electrode 8, and the second electrode 9 is used to apply or receive signals. The thus-created CMUT has no problem in dielectric strength even if driven at 200 V or more, and its leak current is negligibly small.

In this way, a CMUT including a substrate having a through wiring line, a CMUT element unit, and a control circuit is created. The method for creating the CMUT of this example allows a CMUT element to be easily created without a support substrate even if the thickness of the substrate required for the performance is so thin that mechanical strength necessary for the creating process is not satisfied. Moreover, since the method forms high-temperature thermal oxide films with high dielectric strength between the electrodes, the through wiring lines, and the substrate backwiring lines and the substrate, the method provides high electrical reliability and performance of the entire CMUT.

Second Example

The CMUT described in the first example can be applied to subject-information acquisition apparatuses using acoustic waves, such as an ultrasonic diagnostic scanner and an ultrasonic imaging apparatus. The CMUT can receive acoustic waves from a subject and output electrical signals to allow acquisition of subject information that reflects optical characteristic values of the subject, such as an optical absorption coefficient and subject information that reflects a difference in acoustic impedance.

Figure 4A:
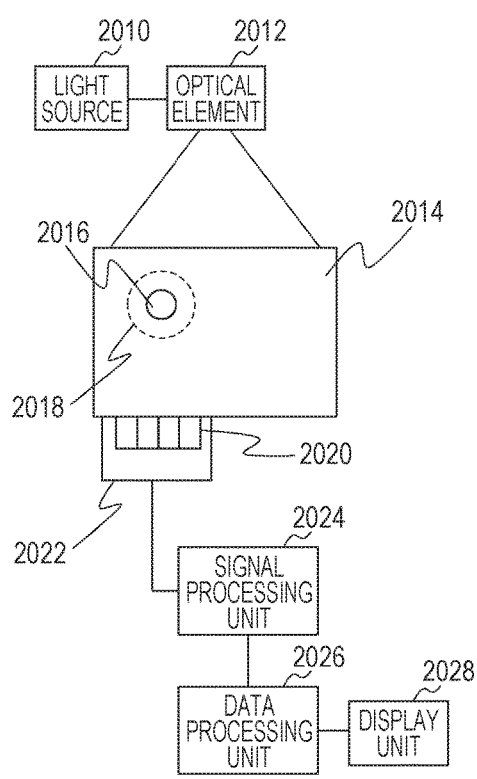
FIG. 4A is a diagram illustrating an application example of the device according the embodiment of the present invention.

FIG. 4A illustrates an example of a subject-information acquisition apparatus using a photoacoustic effect according to an embodiment of the present invention. Pulsed light emitted from a light source 2010 is applied to a subject 2014 via an optical element 2012 including a lens, a mirror, and an optical fiber. A light absorber 2016 in the subject 2014 absorbs the energy of the pulsed light and generates photoacoustic waves 2018, or acoustic waves. A device 2020 including an electromechanical transducer (CMUT) according to an embodiment of the present invention in a probe 2022 receives the photoacoustic waves 2018, converts the photoacoustic waves 2018 to electrical signals, and outputs the electrical signals to a signal processing unit 2024. The signal processing unit 2024 performs signal processing, such as analog-to-digital conversion and amplification, on the input electrical signals, and outputs the processed signals to a data processing unit 2026. The data processing unit 2026 acquires, as image data, subject information (characteristic information that reflects the optical characteristics of the subject, such as an optical absorption coefficient) using the input signals. Here, the signal processing unit 2024 and the data processing unit 2026 are collectively referred to as a processing unit. A display unit 2028 displays images on the basis of the image data input from the data processing unit 2026. Thus, the subject-information acquisition apparatus of this example includes a device according to an embodiment of the present. invention, a light source, and a processing unit. The device receives photoacoustic waves generated from the subject irradiated with light emitted from the light source, converts the photoacoustic waves to electrical signals, acquires subject information using the electrical signal with the processing unit.

Figure 4B:
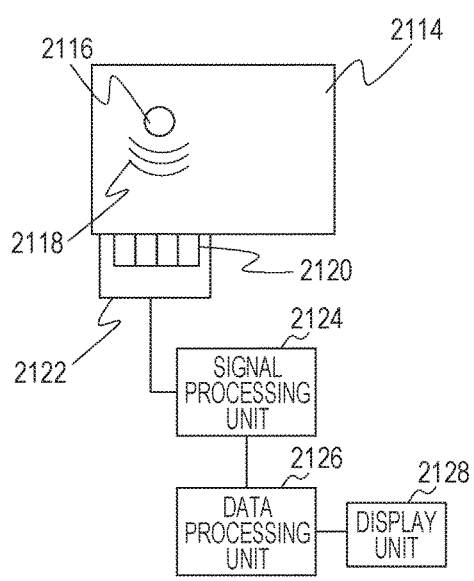
FIG. 4B is a diagram illustrating another application example of the device according the embodiment of the present invention.

FIG. 4B illustrates a subject-information acquisition apparatus using reflection of acoustic waves, such as an ultrasonic echo diagnostic scanner. Acoustic waves transmitted from a device 2120 including an electromechanical transducer (CMUT) according to an embodiment of the present invention in a probe 2122 to a subject 2114 are reflected by a reflector 2116. The device 2120 receives the reflected acoustic waves (reflected waves) 2118, converts the reflected waves to electrical signals, and outputs the electrical, signals to a signal processing unit 2124. The signal processing unit 2124 performs signal processing, such as analog-to-digital conversion and amplification, on the input electrical signals, and output the processed electrical signals to a data processing unit 2126. The data processing unit 2126 acquires, as image data, subject information (characteristic information that reflects a difference in acoustic impedance) using the input signals. The signal processing unit 2124 and the data processing unit 2126 are also collectively referred to as a processing unit. A display unit 2128 displays images on the basis of the image data input from the data processing unit 2126. Thus, the subject-information acquisition apparatus of this example includes a device according to an embodiment of the present invention and a processing unit that acquires subject information using electrical signals output from the device. The device receives acoustic waves from the subject and outputs electrical signals.

The probes 2022 and 2122 may be moved relative to the subject either mechanically or manually by the user including a doctor and an operator (hand-held type). For an apparatus using reflected waves, as illustrated in FIG. 4B, a probe that transmits acoustic waves may be different from a probe that receives reflected waves. Furthermore, an apparatus having both of the functions of the apparatuses in FIG. 4A and FIG. 4B may be provided to acquire both of subject information that reflects the optical characteristics of the subject and subject information that reflects a difference in acoustic impedance. In this case, the device 2020 in FIG. 4A may not only receive photoacoustic waves but also transmit acoustic waves and receive reflected waves.

The above CMUTs can also be used in an external-force measuring apparatus and other equivalent apparatuses. In this case, the CMUTs measure the magnitude of external force applied to the surfaces of the CMUTs using electrical signals coming from the CMUTs.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-262664, filed Dec. 25, 2014, which is hereby incorporated by reference herein in its entirety.

What is claimed is:

1. A device comprising:
   a semiconductor substrate including a first surface and a second surface opposite to the first surface;
   a through wiring line passing through the substrate between the first surface and the second surface;
   electrodes electrically connected to the through wiring line; and
   an insulating film is disposed between the through wiring line and the semiconductor substrate,
   wherein the insulating film is a silicon oxide film, and wherein a silicon nitride film is disposed between the through wiring line and the semiconductor substrate.

2. The device according to claim 1, wherein the device comprises a capacitive micro-machined ultrasonic transducer.

3. A subject-information acquisition apparatus comprising:
   the transducer according to claim 2; and
   a processing unit configured to acquire information on a subject using an electrical signal output from the transducer,
   wherein the transducer receives acoustic waves from the subject and converts the acoustic waves to the electrical signal.

4. The subject-information acquisition apparatus according to claim 3, further comprising:
   a light source,
   wherein the transducer receives photoacoustic waves generated from the subject irradiated with light emitted from the light source and converts the photoacoustic waves to an electrical signal, and
   wherein the processing unit acquires information on the subject using the electrical signal.

5. A subject-information acquisition apparatus comprising:
   the transducer according to claim 2;
   a light source; and
   a processing unit configured to acquire information of a subject using an electrical signal output from the transducer,
   wherein the transducer receives acoustic waves generated from the subject irradiated with light emitted from the light source and converts the acoustic waves to the electrical signal.

6. A measuring apparatus comprising:
   the transducer configured to receive external force according to claim 2,
   wherein the measuring apparatus measures a magnitude of the external force applied to a surface of the transducer using an electrical signal from the transducer.

7. The device according to claim 1, wherein the device comprises a piezoelectric transducer.

8. A subject-information acquisition apparatus comprising:
   the transducer according to claim 7; and
   a processing unit configured to acquire information on a subject using an electrical signal output from the transducer,
   wherein the transducer receives acoustic waves from the subject and converts the acoustic waves to the electrical signal.

9. The subject-information acquisition apparatus according to claim 8, further comprising:
   a light source,
   wherein the transducer receives photoacoustic waves generated from the subject irradiated with light emitted from the light source and converts the photoacoustic waves to an electrical signal, and
   wherein the processing unit acquires information on the subject using the electrical signal.

10. A subject-information acquisition apparatus comprising:
    the transducer according to claim 7;
    a light source; and
    a processing unit configured to acquire information of a subject using an electrical signal output from the transducer, wherein the transducer receives acoustic waves generated from the subject irradiated with light emitted from the light source and converts the acoustic waves to the electrical signal.

11. A measuring apparatus comprising:
the transducer configured to receive external force according to claim 7,
wherein the measuring apparatus measures a magnitude of the external force applied to a surface of the transducer using an electrical signal from the transducer.

12. The device according to claim 1, wherein the silicon nitride film is formed by a LP-CVD method.

13. The device according to claim 1, wherein a thermal oxide layer is disposed only in a part of the first surface or a part of the second surface.

14. The device according to claim 1, wherein the substrate has a thickness of 300 µm or less.

15. A device comprising:
a semiconductor substrate including a first surface and a second surface opposite to the first surface;
a through wiring line passing through the substrate between the first surface and the second surface;
electrodes electrically connected to the through wiring line; and
an insulating film between the through wiring line and the semiconductor substrate, the insulating film being a high dielectric strength film formed at a temperature of 800° C. or higher and being one or more layers of a silicon thermal oxide film formed by thermal oxidation,
wherein a silicon nitride film is disposed between the through wiring line and the semiconductor substrate.

16. The device according to claim 15, wherein the insulating film is one or more layers of a silicon nitride film formed by CVD.

17. The device according to claim 15, wherein the insulating film is heat resistant at least at temperatures less than or equal to 400° C.

18. The device according to claim 15, wherein the substrate has a thickness of 300 µm or less.

* * * * *